US008838241B1

(12) United States Patent
Ness et al.

(10) Patent No.: US 8,838,241 B1
(45) Date of Patent: Sep. 16, 2014

(54) NEUROSTIMULATION CONTROLLED BY ASSESSMENT OF CARDIOVASCULAR RISK

(71) Applicant: Pacesetter, Inc., Sylmar, CA (US)

(72) Inventors: Lanitia Ness, Los Angeles, CA (US); Martin Cholette, Acton, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 13/780,777

(22) Filed: Feb. 28, 2013

(51) Int. Cl.
*A61N 1/00* (2006.01)
*A61N 1/36* (2006.01)

(52) U.S. Cl.
CPC ................................. *A61N 1/36114* (2013.01)
USPC .......................................................... 607/27

(58) Field of Classification Search
USPC .......................................................... 607/27
See application file for complete search history.

(56) References Cited

U.S. PATENT DOCUMENTS

| | | | |
|---|---|---|---|
| 5,058,584 A | 10/1991 | Bourgeois | |
| 5,199,428 A | 4/1993 | Obel et al. | |
| 5,824,021 A | 10/1998 | Rise | |
| 7,010,345 B2 | 3/2006 | Hill et al. | |
| 7,027,856 B2 | 4/2006 | Zhou et al. | |
| 7,218,964 B2 | 5/2007 | Hill et al. | |
| 7,228,167 B2 * | 6/2007 | Kara et al. | 600/509 |
| 7,787,946 B2 * | 8/2010 | Stahmann et al. | 607/3 |
| 7,860,563 B2 | 12/2010 | Foreman et al. | |
| 7,930,017 B1 * | 4/2011 | Fain et al. | 600/509 |
| 2004/0122478 A1 * | 6/2004 | Stadler et al. | 607/17 |
| 2006/0111745 A1 | 5/2006 | Foreman et al. | |
| 2006/0111746 A1 | 5/2006 | Foreman et al. | |

OTHER PUBLICATIONS de Jongste, Mike J.L. et al., "Effects of spinal cord stimulation on myocardial ischaemia during daily life in patients with severe coronary artery disease," Br Heart J. 1994;71:413-418.
De Landsheere, Christian MD et al., "Effect of Spinal Cord Stimulation on Regional Myocardial Perfusion Assessed by Positron Emission Tomography," Am J Cardiol. 1992;69:1143-1149.
Di Pede, Francesco et al., "Long-term effects of spinal cord stimulation on myocardial ischemia and heart rate variabiltity: results of a 48-hour ambulatory electrocardiographic monitoring," Ital Heart J. 2001;2(9):690-695.
Ferrero, Paolo et al., "Spinal cord stimulation affects T-wave alternans in patients with ischaemic cardiomyopathy: a pilot study," Europace. 2008;10:506-508.
Hautvast, Raymond W.M. MD et al., "Effect of Spinal Cord Stimulation on Heart Rate Variability and Myocardial Ischemia in Patients with Chronic Intractable Angina Pectoris—A Prospective Ambulatory Electrocardiographic Study," Clin Cardiol. 1998;21:33-38.

* cited by examiner

*Primary Examiner* — George Manuel

(57) ABSTRACT

Stimulation of a patient's nervous system is controlled based on cardiovascular risk assessment performed by an implantable medical device. For example, an implantable medical device may monitor cardiac electrical activity to detect changes in the ST segment. Upon detection of a certain change in the ST segment, the implantable medical device controls the application of spinal cord stimulation and/or other neurostimulation to cardiac-related sections of the patient's nervous system. In some embodiments, the implantable medical device communicates with a separate neurostimulation device to control the neurostimulation. In some embodiments, the implantable medical device delivers the neurostimulation.

18 Claims, 9 Drawing Sheets

_US 8,838,241 B1_

NEUROSTIMULATION CONTROLLED BY ASSESSMENT OF CARDIOVASCULAR RISK

TECHNICAL FIELD

This application relates generally to implantable medical devices and more specifically, but not exclusively, to controlling neurostimulation based on cardiovascular risk assessment.

BACKGROUND

Spinal cord stimulation (SCS) is a known technique for treating pain. For example, SCS may be used in a pain management scheme to treat neuropathic pain, refractory angina pain, or peripheral vascular disease pain.

In some cases, SCS is applied in response to pain. For example, a patient may trigger the application of SCS (e.g., by actuating a switch of an SCS device) whenever the patient experiences pain.

In some cases, SCS is applied according to a schedule to prevent pain or other symptoms. For example, an SCS device may be programmed to apply SCS for a defined period to time, a defined number of times per day (e.g., for 2 hours, 3 times a day).

It has also been suggested that SCS may be used for cardiac management applications. For example, it has been suggested that SCS may reduce the number of ischemic episodes, shorten ischemic duration, reduce ischemic burden, and mitigate onset of ischemic episode. In patients with ambulatory ischemia who use SCS to prevent angina attacks and as needed to treat angina attacks, SCS has been shown to eliminate ST segment changes. In patients with high arrhythmic risk profiles, SCS has been shown to have an anti-ischemic effect as measured by changes in T-wave alternans (TWA).

SUMMARY

A summary of several sample aspects of the disclosure follows. This summary is provided for the convenience of the reader to provide a basic understanding of such aspects and does not wholly define the breadth of the disclosure. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later. For convenience, the term some aspects may be used herein to refer to a single aspect or multiple aspects of the disclosure. Similarly, the term some embodiments may be used herein to refer to a single embodiment or multiple embodiments.

The disclosure relates in some aspects to proactively controlling neurostimulation to treat one or more cardiac conditions (e.g., ischemia, arrhythmia, etc.). Cardiac signals are acquired and processed to assess cardiovascular risk. Depending on the results of the cardiovascular risk assessment, neurostimulation may be triggered and/or adapted to provide immediate treatment to mitigate the cardiovascular risk. For example, neurostimulation signals may be applied to one or more nerves to impact sympathetic response and/or parasympathetic response. This, in turn, will improve cardiac function of the patient in some cases. For example, acute neurostimulation may be employed to reduce ST segment shifts, T-wave alternans (TWA), and infarct size. Thus, neurostimulation may be used to treat ischemia and angina pain and to mitigate the risk of cardiac damage. Moreover, neurostimulation may be used to treat bradycardia and atrial tachyarrhythmias including atrial fibrillation, and to treat other cardiac conditions.

By proactively preventing cardiac conditions using neurostimulation in accordance with the teachings here, the number and severity of cardiac detrimental episodes experienced by a patient may be reduced, and the chance or magnitude of cardiac infarction may be reduced, thereby preventing damage to the overall health of the patient. Advantageously, these results may be achieved while requiring less intervention by the patient and/or a medical provider.

In some embodiments, neurostimulation is adapted based on reassessment of cardiovascular risk. For example, after triggering and/or adapting the application of neurostimulation, cardiovascular risk is reassessed to determine whether and/or the extent to which the neurostimulation mitigated the cardiovascular risk. Based on this reassessment, the neurostimulation is adapted in an attempt to improve the therapy.

In some embodiments, neurostimulation and/or cardiac sensing are controlled to prevent neurostimulation signals from adversely affecting cardiac sensing operations. For example, neurostimulation may be disabled during cardiac sensing. As another example, cardiac sensing may be disabled during the application of neurostimulation.

In view of the above, in some aspects, an implantable medical device comprises: a receiver circuit configured to acquire cardiac signals of a patient; and a processing circuit configured to assess cardiovascular risk based on the acquired cardiac signals, and to control application of (e.g., trigger and/or adjustment at least one parameter of) neurostimulation to the patient based on the assessment of cardiovascular risk, wherein: the receiver circuit is further configured to acquire additional cardiac signals after the neurostimulation is applied to the patient, and the processing circuit is further configured to reassess cardiovascular risk based on the acquired additional cardiac signals, and to adapt neurostimulation to the patient based on the reassessed cardiovascular risk.

In some embodiments, the assessment of cardiovascular risk involves detecting changes in the ST segment. For example, an implantable medical device (e.g., a cardiac management rhythm device) may employ ST segment monitoring to detect ST segment changes, whereby certain changes in the ST segment trigger the application or adjustment of parameters of neurostimulation to treat ischemia and/or other cardiac conditions.

In view of the above, in some aspects, an implantable medical device comprises: a receiver circuit configured to acquire cardiac signals of a patient; and a processing circuit configured to detect a change in an ST segment based on the acquired cardiac signals, and further configured to control application of neurostimulation to the patient based on the detected change in the ST segment.

In some embodiments, an implantable medical device assesses cardiovascular risk and communicates with a separate neurostimulation device to control neurostimulation. The implantable medical device may be coupled to or otherwise utilize circuitry for acquiring cardiac signals that are then processed to assess cardiovascular risk. In addition, the implantable medical device may be coupled to or otherwise utilize circuitry for sending a control signal (e.g., radiofrequency (RF) signals) to the neurostimulation device. As a result of receiving the control signal, the neurostimulation device generates stimulation signals that are applied (e.g., via an implantable stimulation lead) to a patient's nervous system.

In some embodiments, an implantable medical device assesses cardiovascular risk and delivers neurostimulation. The implantable medical device may be coupled to or otherwise utilize circuitry for acquiring cardiac signals that are then processed to assess cardiovascular risk. In addition, the implantable medical device may be coupled to or otherwise utilize circuitry for generating stimulation signals that are applied to a patient's nervous system.

BRIEF DESCRIPTION OF THE DRAWINGS

These and other aspects of the disclosure will be more fully understood when considered with respect to the following detailed description, the appended claims, and the accompanying drawings, wherein:

Figure 1:
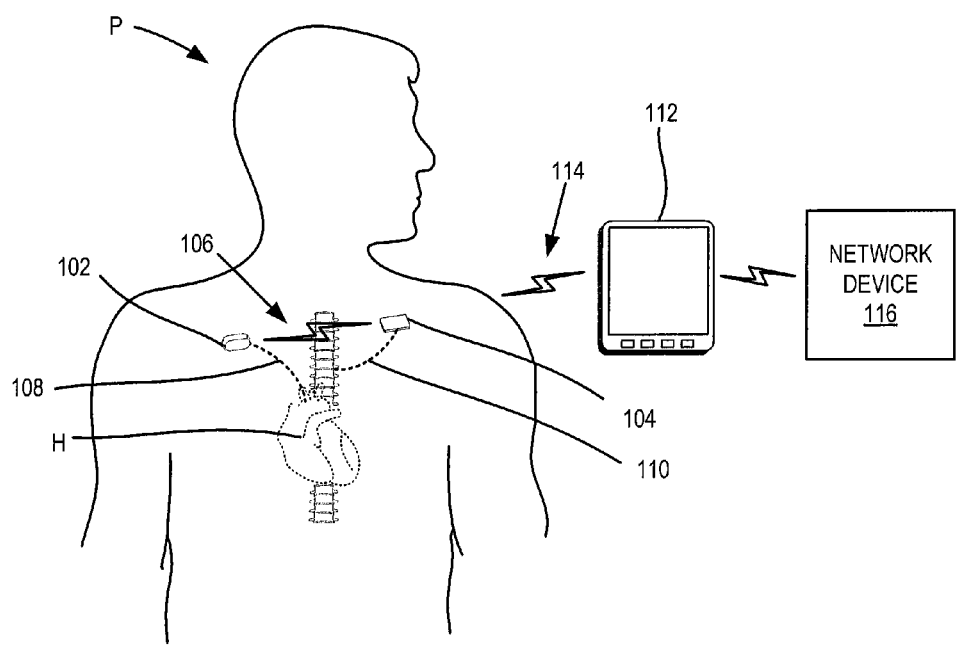
FIG. 1 is a simplified diagram of an embodiment of a medical system comprising an implanted medical device in communication with an implanted neurostimulation device to control neurostimulation for a patient.

In accordance with common practice, the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

FIG. 1 is a simplified drawing illustrating an embodiment of a medical system 100 where neurostimulation is controlled based on assessment of cardiovascular risk. An implantable medical device 102 implanted within a patient P communicates with an implantable neurostimulation device 104 also implanted within the patient P. In some embodiments, the devices 102 and 104 communicate with one another via a wireless communication link 106 (as represented by the depicted wireless symbol).

In the illustrated example, the device 102 is an implantable cardiac device that includes or is coupled to one or more implantable leads 108 that are routed to the heart H of the patient P. The device 102 will typically be a cardiac rhythm management device, a pacemaker, an implantable cardioverter defibrillator, or some other similar device. It should be appreciated, however, that the device 102 may take other forms.

The device 102 is capable of monitoring one or more cardiac conditions (e.g., by acquiring and processing cardiac signals) of the patient P. In accordance with the teachings herein, the device 102 is configured to assess cardiovascular risk to the patient P by analyzing the monitored cardiac condition(s). In the event the risk meets or exceeds a defined criterion (or defined criteria), the device 102 controls the application of neurostimulation in an attempt to mitigate the cardiovascular risk. For example, the device 102 may monitor for changes in the ST segment of an intracardiac electrogram (IEGM) acquired by the device 102. If the change in the ST segment exceeds a threshold amount (e.g., indicating that the patient is experiencing an episode of ischemia), the device 102 may control spinal cord stimulation in an attempt to lessen or terminate the ischemic episode. For example, the device 102 may transmit a control signal to the device 104 (e.g., by sending a message via RF signaling) requesting that the device 104 commence neurostimulation or adapt ongoing neurostimulation.

Controlling the application of neurostimulation may thus involve different types of operations in different embodiments and/or therapy scenarios. In some cases, controlling the application of neurostimulation involves triggering neurostimulation. For example, neurostimulation may be commenced if there is an unacceptable level of cardiovascular risk.

In some cases, controlling the application of neurostimulation involves selecting (e.g., adjusting) at least one parameter used for neurostimulation. For example, in patients with angina, the neurostimulation may already be on to prevent an ischemia/angina episode. Thus, depending on the results of a cardiovascular risk assessment, the ongoing neurostimulation may be adapted in an attempt to optimize the treatment for the patient. In particular, patients employing conventional manually-activated neurostimulation devices may turn on a higher intensity of neurostimulation (compared to prophylactic uses) during an angina episode to treat the angina pain and shorten the episode. Thus, in a system constructed in accordance with the teachings herein, if an angina occurs during a time when the neurostimulation is on for prophylactic treatment, the system may automatically increase the intensity of neurostimulation to help treat the pain.

In the illustrated example, the device 104 is an implantable neurostimulation device that includes or is coupled to one or more implantable leads 110 that are routed to the nervous system of the patient P. The device 104 may be configured and implanted to stimulate the spinal cord, the vagus nerve, baroreceptors, subcutaneous nerves, or other sections of the nervous system of the patient P.

Upon receipt of an appropriate control signal (e.g., a trigger signal) from the device 102, the device 104 generates a stimulation signal (e.g., one or more pulses) and applies that stimulation signal to the designated section(s) of the nervous system. In some implementations, one or more of the stimulation signal characteristics, the stimulation timing, and the stimulation target areas may be specified by the control signal and/or other by other messages sent to the device 104.

By applying stimulation to appropriate sections of the nervous system, cardiac function for the patient may be improved (e.g., an ischemic episode terminated or lessened). In this way, the cardiovascular risk to the patient is proactively mitigated whenever certain cardiac conditions are detected by the device 102. Accordingly, the system 100 may be more effective at improving a patient's health compared to conventional devices where stimulation is applied according to a rigid schedule (e.g., where treatment may not be provided for episodes that fall outside of the stimulation window of the schedule). In addition, the system 100 may be more effective at improving a patient's health compared to conventional devices where stimulation is applied as a result of patient triggers when the patient is experiencing pain (e.g., where treatment may not be provided for episodes that do cause an appreciable level of pain).

FIG. 1 also illustrates that the device 102 and/or the device 104 may communicate with an external device 112. An implanted device and the external device 112 may communicate with one another via a wireless communication link 114 (as represented by the depicted wireless symbol).

The external device 112 may take various forms. For example, the external device 112 may be a base station, a programmer, a home safety monitor, a personal monitor, a follow-up monitor, a wearable monitor, or some other type of device that is configured to communicate with an implanted device.

The communication link 114 may be used to transfer information between the internal and external devices in conjunction with various applications such as remote programming, remote home-monitoring, clinical visits, data acquisition, remote follow-up, and portable or wearable patient monitoring/control systems. For example, information may be transferred between the internal and external devices when the patient P is at a location that is relatively close to the external device 112. Here, information transfers may be invoked upon command, at designated times, or in some other manner.

The external device 112 may send information it receives from an implanted device to another device (e.g., that may provide a more convenient means for a physician or other personnel to program an implanted device or review information uploaded from an implanted device), and vice versa. For example, the external device 112 may send information from the device 102 to a network device 116 (e.g., via a web server). In this way, monitoring personnel (e.g., a physician) may remotely access the information (e.g., by accessing a website). The monitoring personnel may then review the information uploaded from the implantable device to determine whether medical intervention is warranted. Conversely, personnel may use the network device 116 to program one or both of the implanted devices (e.g., to program detection parameters, to program neurostimulation parameters, to directly control neurostimulation, etc.).

Figure 2:
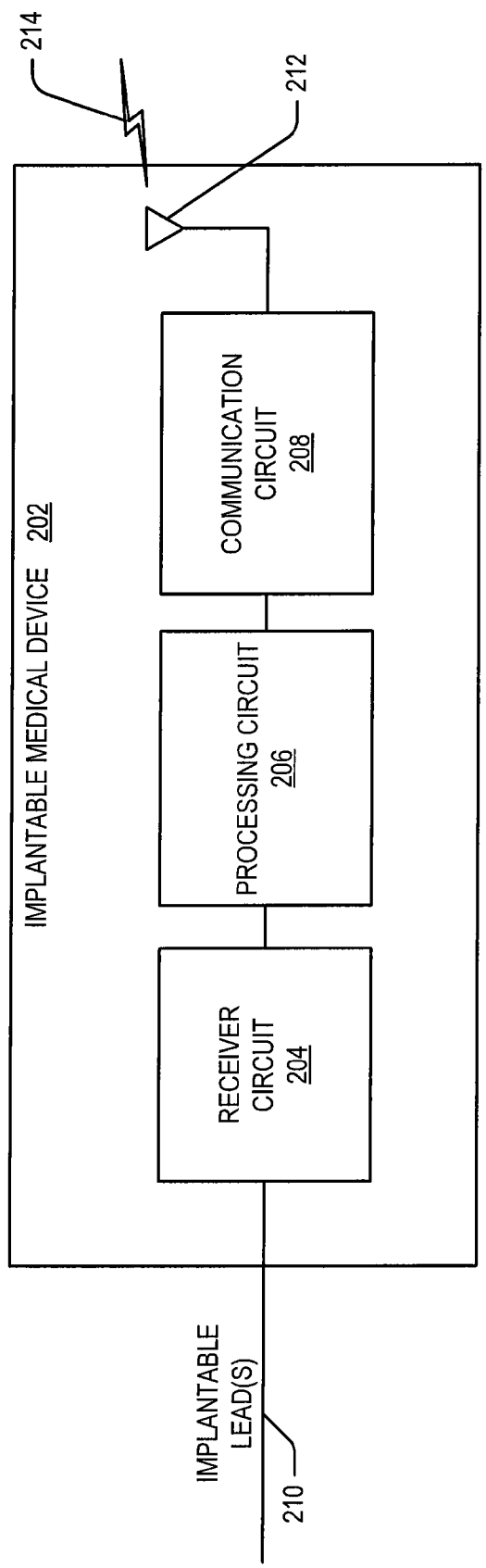
FIG. 2 is a simplified block diagram of an embodiment of an implantable medical device that assesses cardiovascular risk to control neurostimulation for a patient.

FIG. 2 illustrates a simplified example of an embodiment of an implantable medical device 202 configured to control neurostimulation based on assessment of cardiovascular risk. The device 202 includes a receiver circuit 204 for receiving cardiac signals, a processing circuit 206 for assessing cardiovascular risk based on the received cardiac signals, and a communication circuit 208 for transmitting a control signal to control neurostimulation by a neurostimulation device (not shown in FIG. 2).

In the example of FIG. 2, the receiver circuit 204 is coupled to one or more implantable cardiac leads (hereafter referred to for convenience as "implantable lead 210") to detect cardiac signals. The implantable lead 210 may, in turn, be routed from the implantable medical device 102 through the patient's body and implanted within and/or on the heart. It should be appreciated that other techniques (e.g., pressure sensing, far-field sensing, etc.) may be employed to acquire cardiac-related signals in other embodiments.

The receiver circuit 204 may comprise, for example, at least one: sense amplifier, threshold detector, or IEGM processing component. Examples of these components are described in more detail below in conjunction with FIGS. 8 and 9.

The processing circuit 206 processes the signals received by the receiver circuit 204 to make cardiovascular risk assessments. In some aspects, assessment of cardiovascular risk involves assessing at least one of: ischemia, arrhythmia, shift in autonomic tone, or some other cardiac condition. Accordingly, the processing circuit 206 may analyze received cardiac signals (e.g., in the form of IEGMs) to detect whether any of these cardiac conditions are present and, if so, the severity of each cardiac condition.

Various attributes of cardiac signals or cardiac events may be used to detect a cardiac condition. For example, assessment of cardiovascular risk may comprise at least one of: detecting a change in an ST segment, detecting cardiac rate variability, detecting TWA, detecting cardiac ectopy, detecting a change in QRS morphology, detecting a change in left-right chamber synchrony, or detecting some other cardiac signal attribute or cardiac event.

As an example of the above, ischemia detection may involve detecting a change in the level of the ST segment (e.g., ST segment depression). Accordingly, the processing circuit 206 may analyze IEGM data or other information that is representative of the ST segment over time to determine whether there has been a change in the ST segment.

The processing circuit 206 conducts the cardiovascular risk assessments to determine whether to control neurostimulation. In some aspects, this assessment involves determining whether a detected cardiac condition or detected conditions (e.g., ischemia, arrhythmia, shift in autonomic tone, etc.) is/are severe enough to warrant neurostimulation and/or warrant an adjustment of at least one neurostimulation parameter. As discussed above, such an assessment may involve analysis of one or more cardiac attributes (e.g., ST segment, rate variability, TWA, ectopy, change in morphology, left-right synchrony, etc.).

The assessment of cardiovascular risk may take into account the magnitude and/or the frequency of occurrence of a cardiac condition. For example, a change in a parameter (e.g., average or maximum ST segment shift over a number of beats) may be compared to at least one threshold. As another example, the processing circuit may keep track of the number of times a parameter exceeds a threshold over a period of time. In some cases, detection of different magnitudes may initiate different operations. For example, detection of a relatively large change may trigger neurostimulation and/or trigger adjustment of a neurostimulation parameter regardless of the duration of the change. Conversely, detection of a large number of small changes (which would not individually trigger neurostimulation) over a defined period of time could also trigger neurostimulation and/or trigger adjustment of a neurostimulation parameter in some cases.

In the event the assessment of cardiovascular risk indicates that neurostimulation is warranted and/or should be adapted, the processing circuit 206 generates an indication to control the neurostimulation. This may involve generating a signal, sending a message, setting a variable, or some other suitable action. In the example, of FIG. 2, the processing circuit 206 provides the control indication to the communication circuit 208 to signal the communication circuit to transmit a signal that controls the neurostimulation. For example, as a result of receiving a control indication from the processing circuit 206, the communication circuit 208 may transmit a message to the neurostimulation device requesting the initiation of neurostimulation and/or the adjustment of at least one neurostimulation parameter. In the example of FIG. 2, the communication circuit 208 (comprising an RF transmitter and RF receiver) transmits an RF telemetry signal via an antenna 212 as represented by a signaling waveform 214. In this case, the RF signal (e.g., comprising a message) serves as a neurostimulation control (e.g., trigger).

The RF signal is received by a neurostimulation device (e.g., the device 104 of FIG. 1) implanted in the patient. Receipt of the RF signal causes the neurostimulation device to generate a neurostimulation signal that is applied to the nervous system of the patient as discussed herein.

In some embodiments, the controlling of neurostimulation also involves specifying how neurostimulation is to be applied. For example, the control signal and/or some other signal may specify the characteristics of the neurostimulation signal to be used, the timing of the neurostimulation, and the neurostimulation sites. Examples of the characteristics of the neurostimulation signal include amplitude, frequency, and pulse shape. The neurostimulation sites may be specified in cases where more than one neurostimulation electrode (e.g., on one or more implantable leads) is available for use. Thus, depending on the severity or form of cardiovascular risk, a different number and/or a different group of electrodes may be used for the neurostimulation.

In other embodiments, the manner in which neurostimulation is to be applied may be specified in other ways. For example, neurostimulation parameters may be predefined (e.g., programmed into the neurostimulation device during manufacture) or downloaded from an external device (e.g., a programmer) into the neurostimulation device.

While FIG. 2 illustrates an example where the communication circuit 208 transmits a control indication, it should be appreciated that a communication circuit may send a control indication to a neurostimulation device in other ways. For example, in embodiments where the implantable medical device 202 is coupled to the neurostimulation device via an electrical conductor or optical cable, a control indication may be sent via one of these couplings.

In some embodiments, action may be taken to avoid concurrent neurostimulation and cardiac signal acquisition. For example, the processing circuit 206 may be configured to control the receiver circuit 204 and/or the application of the neurostimulation to prevent acquisition of cardiac signals during neurostimulation. In this way, cardiac signals may be acquired without interference from neurostimulation signals.

In some cases, the acquisition of cardiac signals is disabled whenever neurostimulation is in progress. For example, the processing circuit 206 may be configured to control the receiver circuit 204 to disable the acquisition of the cardiac signals (or ignore acquired signals) for a period of time after the processing circuit 206 has triggered neurostimulation. In this case, the processing circuit 206 may maintain information indicative of how long the neurostimulation will last (e.g., as specified by the processing circuit 206 or as predefined). Consequently, the processing circuit 206 is able to disable cardiac sensing for the appropriate period of time.

As another example, the receiver circuit 204 may be configured to detect neurostimulation signals. In this case, either the receiver circuit 204 and/or the processing circuit 206 may be configured to disable the acquisition of the cardiac signals (or ignore acquired signals) as a result of the detection of the neurostimulation signals.

In some cases, neurostimulation is disabled whenever the acquisition of cardiac signals is in progress. For example, the processing circuit 206 may be configured to delay the triggering of neurostimulation until cardiac signal acquisition is completed. As another example, the processing circuit 206 may be configured to communicate with a neurostimulation device via the communication circuit 208 to request the neurostimulation device to disable neurostimulation during acquisition of the cardiac signals.

Figure 3:
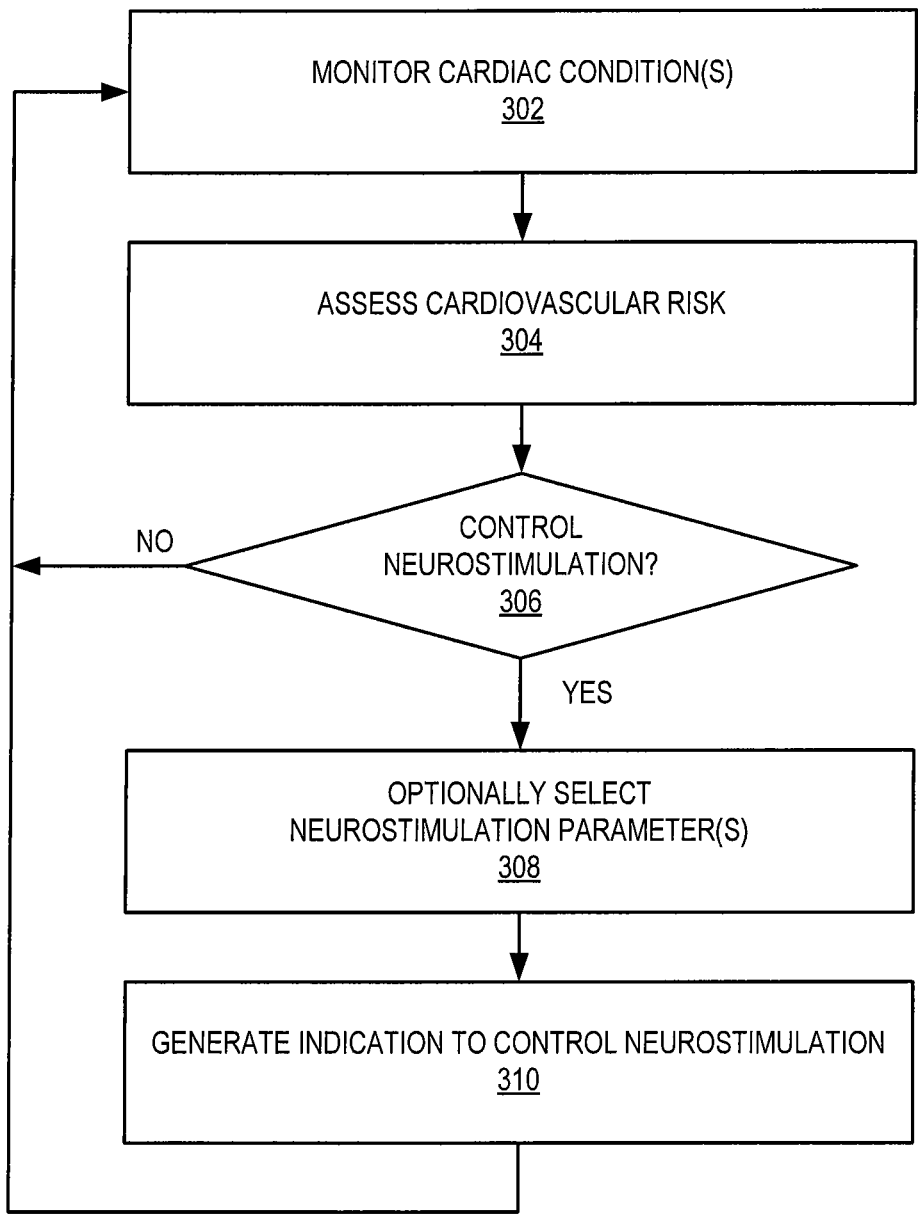
FIG. 3 is a simplified flowchart of an embodiment of operations that may be performed in conjunction with assessing cardiovascular risk and controlling neurostimulation for a patient.

With the above in mind, an overview of operations that may be performed (e.g., by an implantable medical device) to control neurostimulation based on assessment of cardiac risk will be treated with reference to the flowchart of FIG. 3. For convenience, the operations of FIG. 3 (or any other operations discussed or taught herein) may be described as being performed by specific components (e.g., the components of FIG. 2 or FIG. 7). It should be appreciated, however, that these operations may be performed by other types of components and may be performed using a different number of components. It also should be appreciated that one or more of the operations described herein may not be employed in a given implementation.

As represented by block 302 of FIG. 3, one or more cardiac conditions of the patient are monitored. This may involve, for example, acquiring cardiac information continuously (e.g., on a beat-by-beat basis), periodically (e.g., once per minute or hour), or in some other manner.

As represented by blocks 304 and 306, cardiovascular risk is assessed to determine whether to control (e.g., trigger and/or adapt) neurostimulation. As discussed above, this may involve characterizing a high-level event (e.g., ischemia, arrhythmia, shift in autonomic tone, etc.) and/or characterizing underlying cardiac attributes (e.g., ST segment, rate variability, TWA, ectopy, change in morphology, left-right synchrony, etc.).

In the event neurostimulation is not controlled at block 306, the operational flow proceeds back to blocks 302 and 304 whereby the implantable medical device continues monitoring cardiac conditions and assessing cardiovascular risk.

As represented by block 308, in the event neurostimulation is controlled at block 306, one or more neurostimulation parameters may be selected. This may involve, for example, specifying when neurostimulation is to occur, and specifying the form of the neurostimulation signals (e.g., amplitude, frequency components, periodicity, wave shape, etc.).

As represented by block 310, the implantable medical device generates an indication to control the neurostimulation. In embodiments that employ an implantable medical device along a separate neurostimulation device for generating the neurostimulation signal, the indication may comprise a transmitted signal (e.g., an RF signal, an electrical signal, an optical signal, etc.). In embodiments where a single implantable medical device assesses cardiac risk and generates the neurostimulation signal, the indication may comprise a signal, a message, writing to a memory location in a memory device, or some other suitable form of indication.

Figure 4:
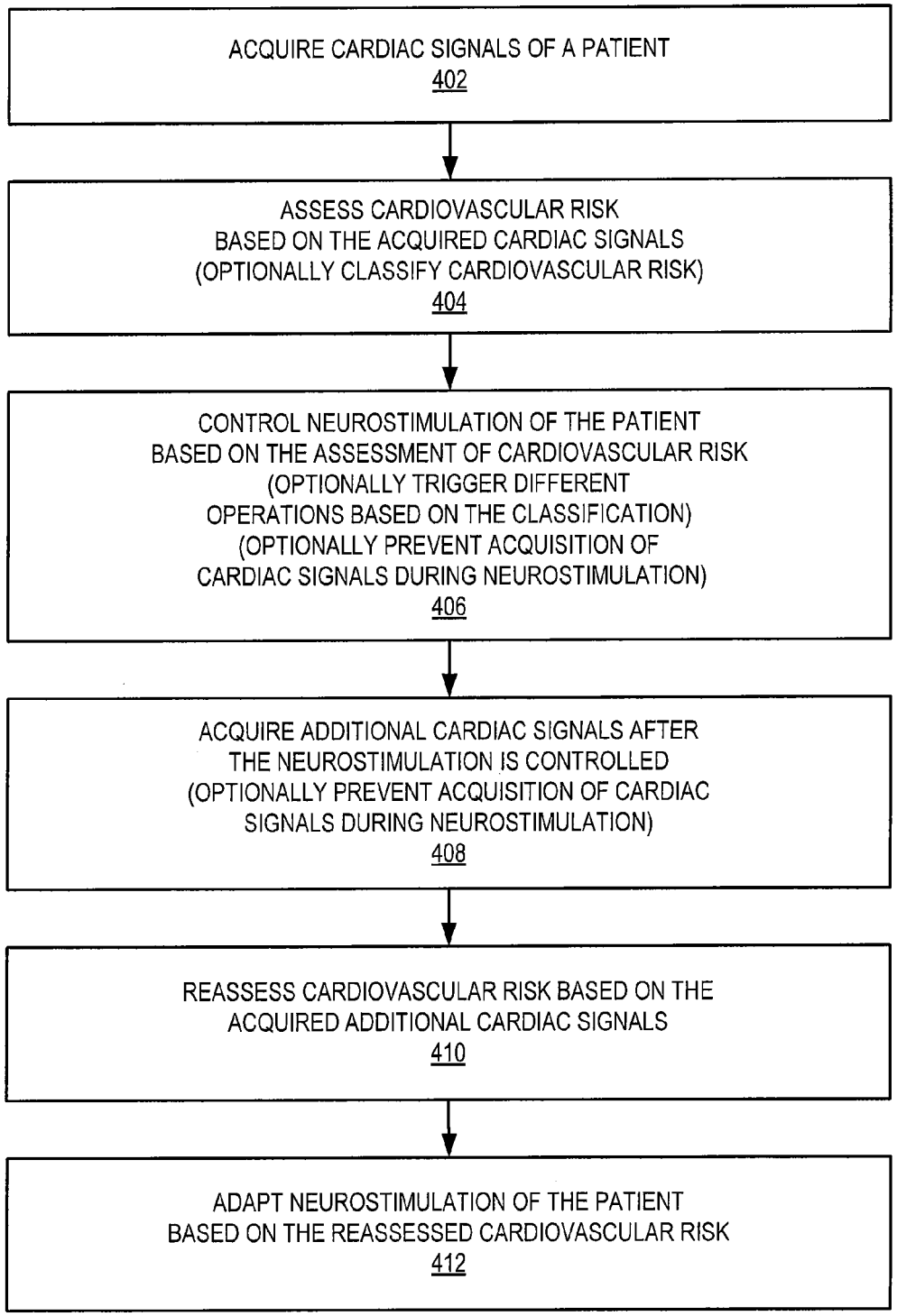
FIG. 4 is a simplified flowchart of an embodiment of operations that may be performed in conjunction with adapting neurostimulation for a patient.

In some embodiments, cardiovascular risk is repeatedly reassessed to adapt the neurostimulation over time. In this way, the best possible neurostimulation may be provided for a patient at a given point in time. As a specific example, ST segment monitoring may be used to objectively quantify the long-term effectiveness of neurostimulation intervention. In particular, changes in the number of ST segments indicative of ischemia episodes and the duration of the episodes may be measured and used to adapt the intervention (and optionally reported to an external device to provide an indication of the reduced ischemia to an attending physician). FIG. 4 illustrates an embodiment of operations that may be employed to provide such an adaptable neurostimulation scheme.

As represented by block 402 of FIG. 4, cardiac signals of a patient are acquired. For example, an initial set of IEGM data corresponding to a given amount of time may be acquired and stored in a memory device.

As represented by block 404, cardiovascular risk is assessed based on the acquired cardiac signals. As discussed herein, in some cases, the assessment of cardiovascular risk comprises at least one of: detecting ischemia, detecting arrhythmia, or detecting a shift in autonomic tone. Also, in some cases, the assessment of cardiovascular risk comprises at least one of: detecting a change in an ST segment, detecting cardiac rate variability, detecting T-wave alternans, detecting cardiac ectopy, detecting a change in QRS morphology, or detecting a change in left-right chamber synchrony.

In some embodiments, the assessment of cardiovascular risk comprises classifying cardiovascular risk according to a plurality of cardiovascular risk levels. As one example, the current cardiovascular risk to a patient (e.g., as indicated by the current ST segment shift) may be characterized as low risk, medium risk, or high risk. As discussed in more detail below, different methods of treatment may thus be invoked depending on the current level of risk to the patient.

In some cases, at least one of the risk levels is associated with notifying the patient of cardiovascular risk. For example, a patient may not be notified in cases of low or medium risk, but may be notified in cases of high risk. Such notification may be accomplished in various ways including, for example, sending a message to an external device, activating a mechanical device (e.g., a vibrating device) in the implantable medical device, or triggering a high level of neurostimulation that is perceivable by the patient.

In some cases, different risk levels may be associated with different neurostimulation perception levels. For example, at least one of the risk levels may be associated with the application of neurostimulation that is not perceivable by the patient; while at least one other one of the risk levels may be associated with the application of neurostimulation that is perceivable by the patient. Accordingly, under non-urgent conditions (e.g., low to medium cardiovascular risk), the magnitude and/or duration of the neurostimulation may be maintained at a level that is not perceivable by the patient, thereby insuring that the treatment is non-invasive. In contrast, under urgent conditions (e.g., high cardiovascular risk), the magnitude and/or duration of the neurostimulation may be maintained at whatever level is necessary to mitigate the risk, irrespective of whether the neurostimulation is perceivable by the patient As represented by block 406, neurostimulation to the patient is controlled based on the assessment of cardiovascular risk at block 404. As discussed herein, the neurostimulation may comprise spinal cord stimulation, vagus nerve stimulation, baroreceptor stimulation, subcutaneous nerve stimulation, or some other type of stimulation of the patient's nervous system that mitigates cardiovascular risk.

In some embodiments, the controlling of the neurostimulation comprises triggering different neurostimulation operations based on the classification of cardiovascular risk made at block 404. These different neurostimulation operations may involve, for example, use of different neurostimulation signals (e.g., different amplitude, frequency, timing, etc.) and/or use of different neurostimulation electrodes (e.g., at different implant sites).

In some embodiments, action may be taken to prevent the acquisition of cardiac signals during neurostimulation. For example, the triggering of neurostimulation may be delayed or otherwise disabled whenever the acquisition of cardiac signals is in progress. Thus, in an implementation where an implantable medical device is periodically acquiring cardiac signals, the neurostimulation may be scheduled to ensure that it does not occur during a period of cardiac signal acquisition.

As represented by block 408, after the neurostimulation is controlled at block 406, additional cardiac signals are acquired (e.g., in a similar manner as at block 402). For example, another set of IEGM data corresponding to a given amount of time may be acquired and stored in a memory device along with the initial set of IEGM data.

As discussed above, in some embodiments, action may be taken to prevent the acquisition of cardiac signals during neurostimulation. For example, the acquisition of cardiac signals may be disabled in the event neurostimulation is in progress. Thus, in an implementation where an implantable medical device normally acquires cardiac signals on a continual basis (e.g., on a beat-by-beat basis), in the event neurostimulation is in progress, the acquisition of cardiac signal signals may be temporarily disabled or the cardiac signals acquired during this time may be ignored (e.g., discarded).

As represented by block 410, the cardiovascular risk to the patient is reassessed based on the additional cardiac signals acquired at block 408. In this way, the effect of the controlling of the neurostimulation at block 406 may be determined.

The reassessment of cardiovascular risk may be performed in a similar manner as the initial assessment at block 404. For example, the reassessment may comprise at least one of: detecting ischemia, detecting arrhythmia, or detecting a shift in autonomic tone. Also, the reassessment may comprise at least one of: detecting a change in an ST segment, detecting cardiac rate variability, detecting T-wave alternans, detecting cardiac ectopy, detecting a change in QRS morphology, or detecting a change in left-right chamber synchrony.

As represented by block 412, the neurostimulation to the patient may be adapted based on the reassessment of cardiovascular risk made at block 410. For example, if the reassessment shows that the risk has lessened, more aggressive neurostimulation may be indicated. Conversely, if the reassessment shows that the risk has increased, the aggressiveness of the neurostimulation may be reduced or terminated.

Also, the device may maintain records that indicate how the patient has responded to different neurostimulation procedures over time. Consequently, a decision on how the neurostimulation is to be adapted may be based on these records.

As discussed herein, this may involve controlling signal attributes, controlling when neurostimulation is to be performed (e.g., how long to wait between triggers), controlling where to apply neurostimulation, and so on.

The operations of blocks 408-412 may be repeated over time to repeatedly adapt the neurostimulation based on the current cardiovascular risk to the patient. Thus, if a patient's condition worsens, more aggressive neurostimulation may be applied as long as that therapy is improving the health of the patient. Conversely, if a patient's condition improves, neurostimulation may be reduced or terminated. Thus, neurostimulation therapy is automatically adapted to the needs of the patient.

Figure 5:
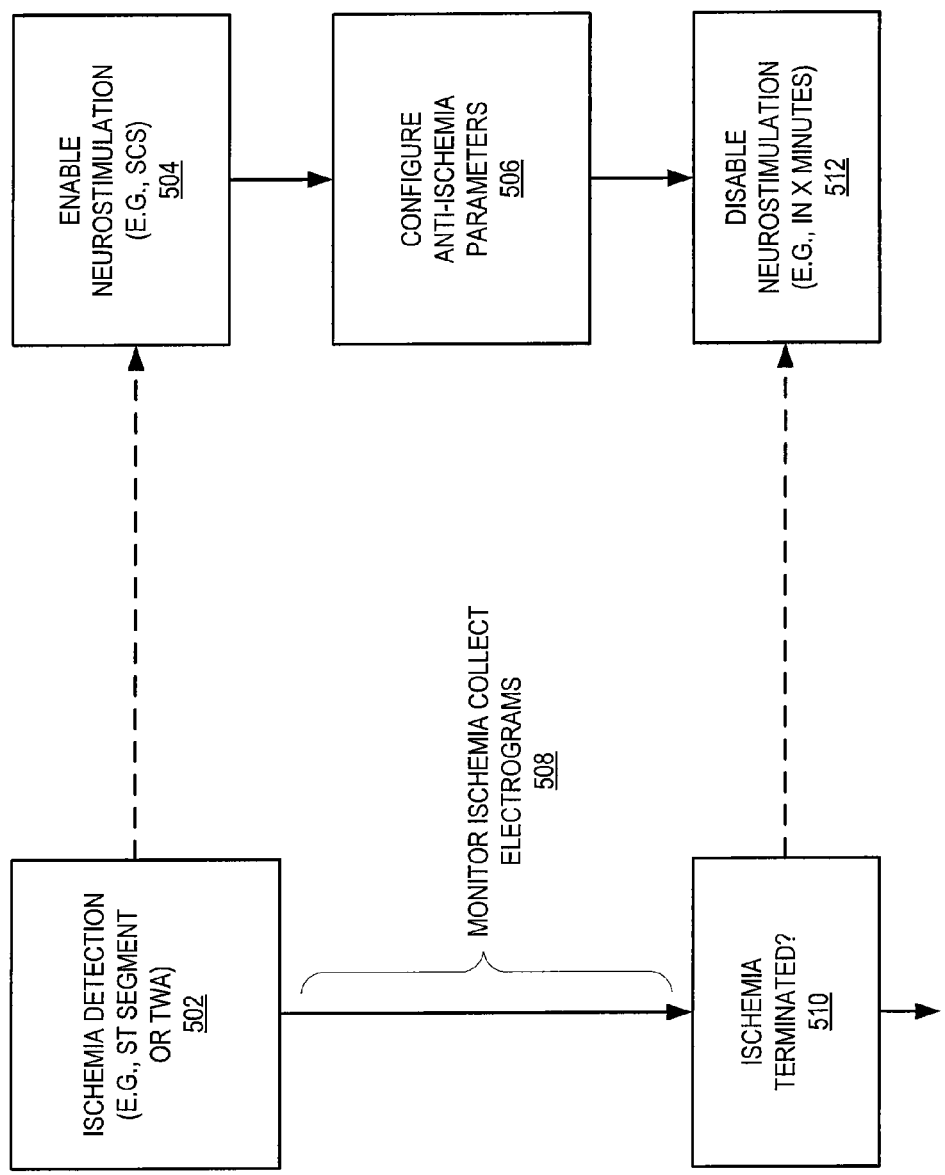
FIG. 5 is a simplified flowchart of an embodiment of operations that may be performed in conjunction with controlling neurostimulation for a patient based on changes in the ST segment.

FIG. 5 illustrates another example of how feedback may be employed to control how and/or when neurostimulation is applied and/or terminated so that the proper amount and/or type of neurostimulation is administered to a patient. This example deals with the specific case of ischemia treatment based on ST segment or TWA detection. It should be appreciated, however, that the described operations may be applicable to other cardiac conditions.

As represented by block 502, ischemia detection is employed to determine when a patient is suffering from an episode of ischemia. As discussed herein this may involve acquiring cardiac signals of the patient and processing the signals to detect at least one change in an ST segment and/or to detect TWA of a certain degree.

As represented by block 504, neurostimulation is enabled based on the detection of ischemia at block 502. For example, spinal cord stimulation may be triggered to treat the ischemia.

As represented by block 506, the proper parameters for treating the ischemia are configured. For example, as discussed herein, the amplitude, frequency, timing, and stimulation sites may be specified based on the severity and/or frequency of the detected ischemia. Neurostimulation based on these parameters is then applied to the patient's nervous system.

As represented by block 508, after ischemia is detected at block 502, the device continues to monitor the ischemia. For example, the device may continue to collect electrograms and process the electrograms to track the changes in the ST segment and/or TWA.

As represented by blocks 510 and 512, once it is determined that the ischemia is terminated (e.g., as a result of the neurostimulation), the neurostimulation is disabled. For example, upon receipt of a signal from an implantable medical device indicating that neurostimulation is to be stopped, an implantable neurostimulation device may disable the neurostimulation within a defined period of time (e.g., X minutes).

Figure 6:
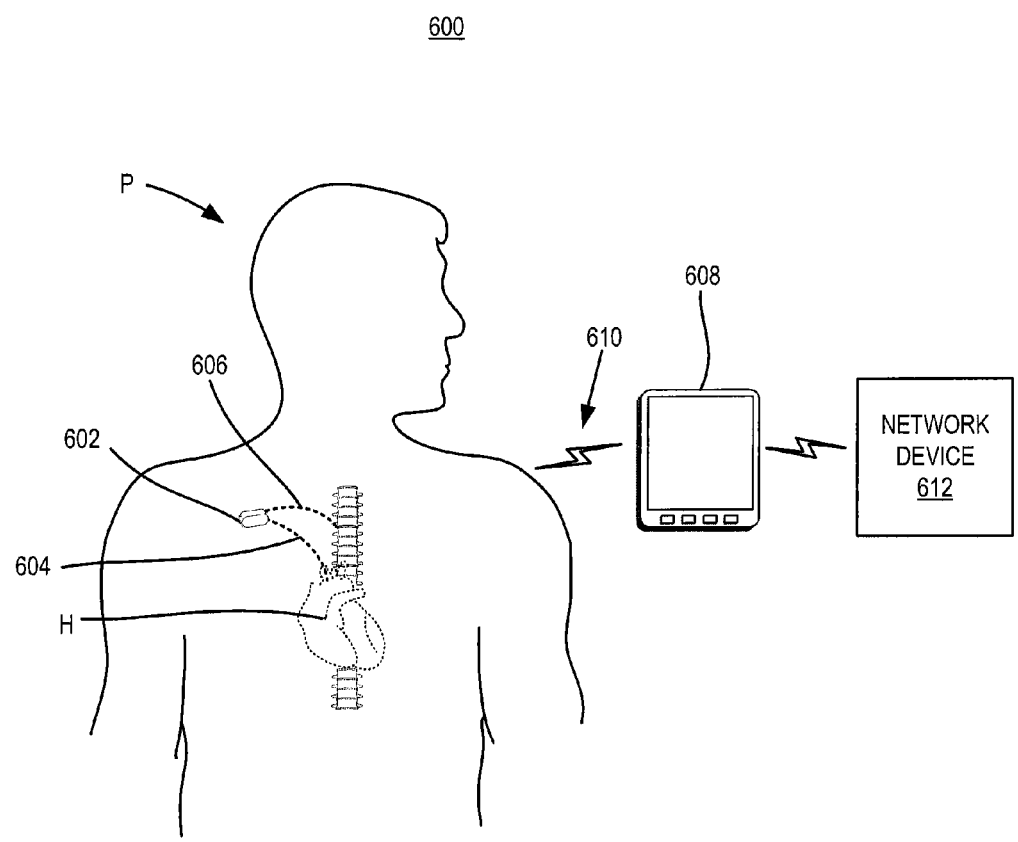
FIG. 6 is a simplified diagram of an embodiment of an implanted medical device that provides neurostimulation for a patient.
Figure 7:
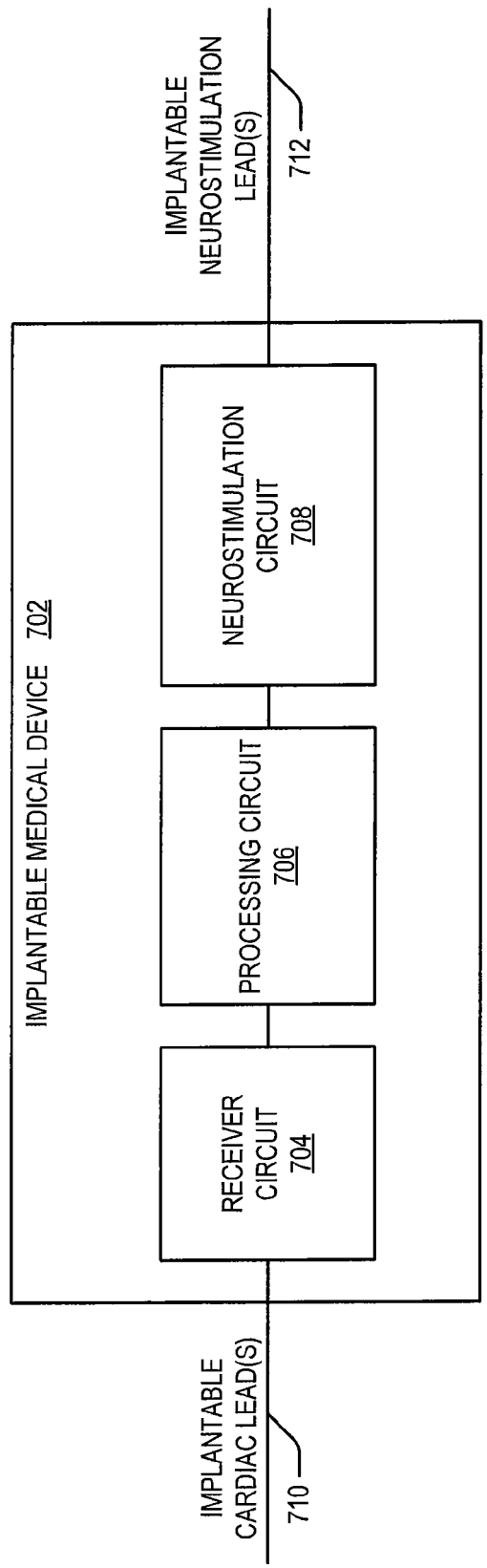
FIG. 7 is a simplified block diagram of an embodiment of an implantable medical device that generates a neurostimulation signal.

Referring now to FIGS. 6 and 7, in some embodiment a single implantable device includes functionality for assessing cardiovascular risk and for generating neurostimulation signals.

FIG. 6 is a simplified drawing illustrating an embodiment of a medical system 600 where an implantable medical device 602 that generates neurostimulation signals is implanted within a patient P. In the illustrated example, the device 602 is an implantable cardiac device that includes or is coupled to one or more implantable cardiac leads 604 that are routed to the heart H of the patient P. The device 602 may be a cardiac rhythm management device, a pacemaker, an implantable cardioverter defibrillator, or some other similar device. It should be appreciated that the device 602 may take other forms.

The device 602 is capable of monitoring one or more cardiac conditions (e.g., by acquiring and processing cardiac signals) of the patient P. In accordance with the teachings herein, the device 602 is configured to assess cardiovascular risk to the patient P by analyzing the monitored cardiac condition(s). In the event the risk meets or exceeds a defined criterion (or defined criteria), the device 602 controls neurostimulation in an attempt to mitigate the cardiovascular risk.

In this embodiment, the device 602 includes or is coupled to one or more implantable neurostimulation leads 606 that are routed to the nervous system of the patient P. For example, the device 602 and the neurostimulation lead(s) 606 may be configured and implanted to stimulate the spinal cord, the vagus nerve, baroreceptors, subcutaneous nerves, or other sections of the nervous system of the patient P. When neurostimulation is triggered, the device 602 generates a neurostimulation signal that is coupled to the designated section(s) of the nervous system via the neurostimulation lead(s) 606.

FIG. 6 also illustrates that the device 602 may communicate with an external device 608. The device 602 and the external device 608 may communicate with one another via a wireless communication link 610 (as represented by the depicted wireless symbol). The external device 608 may take various forms (e.g., as discussed above in conjunction with FIG. 1). Also as discussed above, the external device 608 may send information it receives from the device 602 to another device, and vice versa. For example, the external device 608 may send information from the device 602 to a network device 612.

FIG. 7 illustrates a simplified example of an embodiment of an implantable medical device 702 configured to generate neurostimulation signals based on assessment of cardiovascular risk. The device 702 includes a receiver circuit 704 for receiving cardiac signals, a processing circuit 706 for assessing cardiovascular risk based on the received cardiac signals, and a neurostimulation circuit 708 for generating neurostimulation signals.

The receiver circuit 704 may be similar to the receiver circuit 204 described above at FIG. 2. For example, the receiver circuit 704 may be coupled to one or more implantable cardiac leads (hereafter referred to for convenience as "implantable lead 710") to detect cardiac signals. In addition, the receiver circuit 704 may comprise, for example, at least one: sense amplifier, threshold detector, or IEGM processing component.

The processing circuit 706 may be similar to the processing circuit 706 described above. The processing circuit 706 processes the signals received by the receiver circuit 704 to make cardiovascular risk assessments. In addition, the processing circuit 706 determines whether to control neurostimulation based on the cardiovascular risk assessment. In the event the assessment of cardiovascular risk indicates that neurostimulation is warranted or should be adapted, the processing circuit 706 generates an indication to control the neurostimulation. This may involve generating a signal, sending a message, setting a variable, or some other suitable action. The processing circuit 706 provides the control indication to the neurostimulation circuit 708 to initiate neurostimulation, if needed. Also, the processing circuit 706 may configure the neurostimulation circuit 708 to control the manner in which stimulation is provided (e.g., by specifying signal attributes, signal timing, and electrode configurations as discussed herein).

The neurostimulation circuit 708 includes a signal generator (not shown) for generating the neurostimulation signals. The neurostimulation circuit 708 is also coupled to one or more implantable neurostimulation leads 712, whereby generated neurostimulation signals are induced at the designated stimulation sites under the control of the processing circuit 706 (e.g., appropriate neurostimulation signals are generated as a result of receiving a trigger indication from the processing circuit 706).

Figure 8:
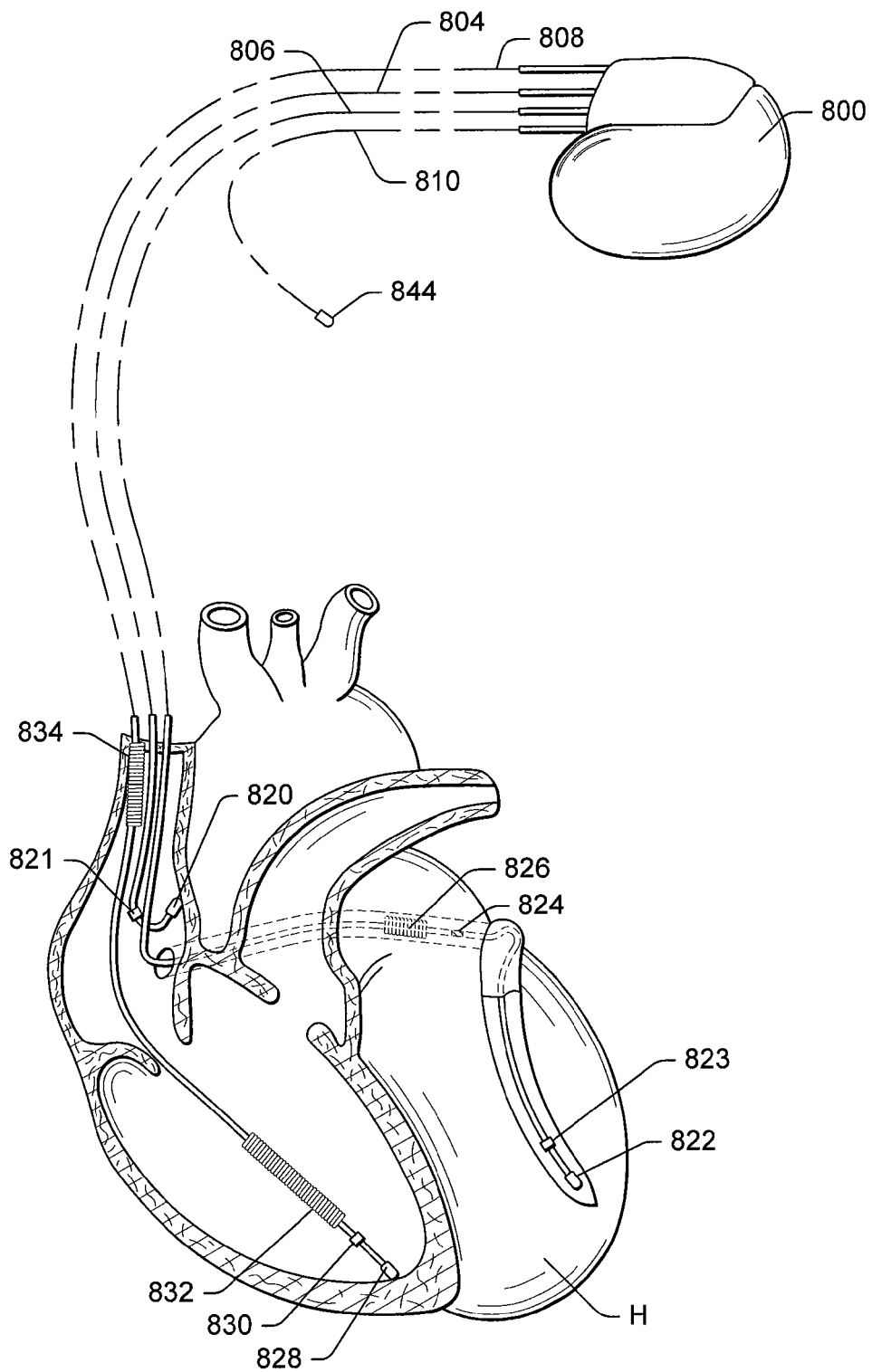
FIG. 8 is a simplified diagram of an embodiment of an implantable stimulation device in electrical communication with one or more leads implanted in a patient's heart for sensing conditions in the patient, delivering therapy to the patient, or providing some combination thereof.
Figure 9:
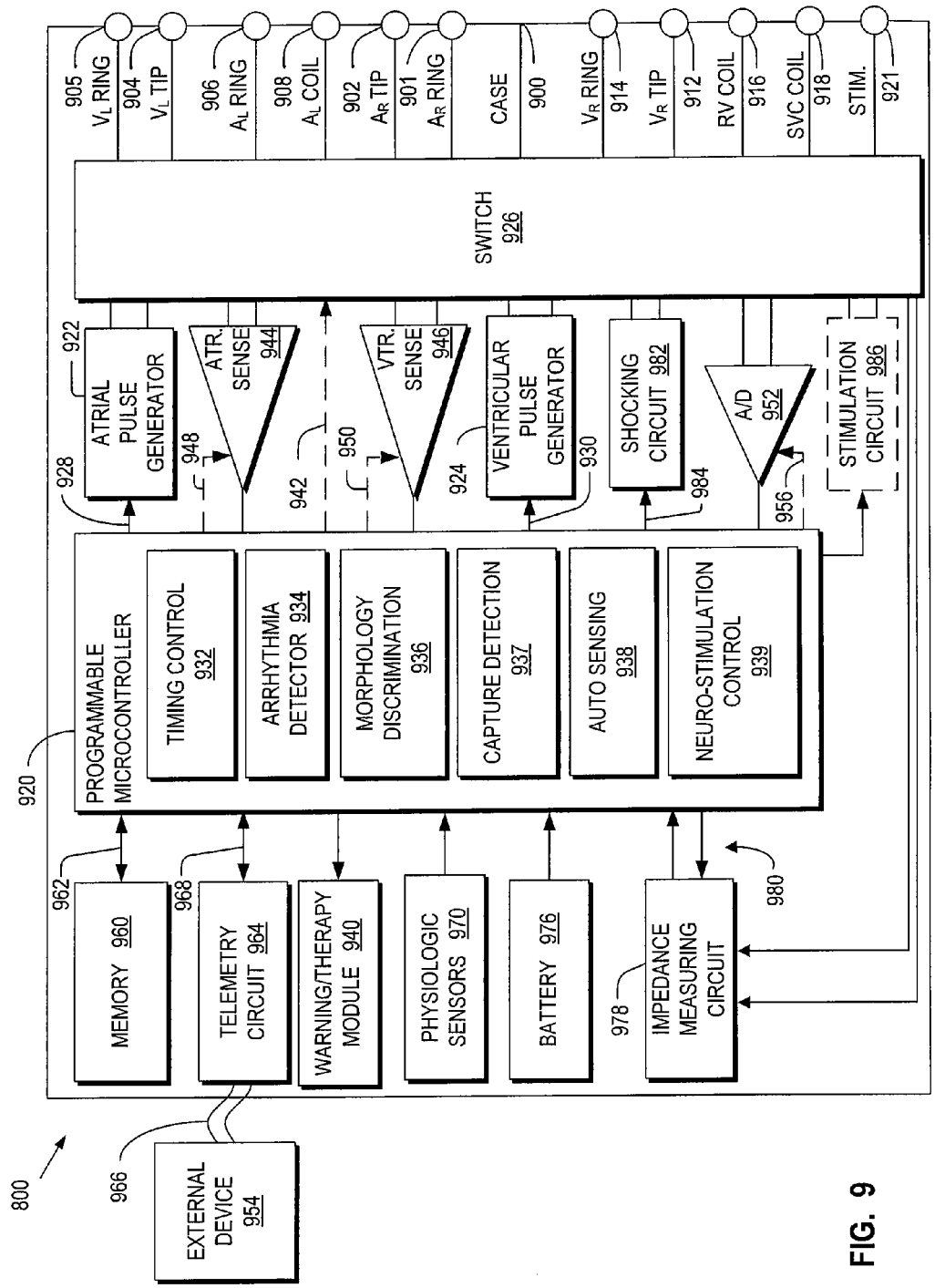
FIG. 9 is a simplified functional block diagram of an embodiment of an implantable cardiac device, illustrating basic elements that may be configured to sense conditions in the patient, deliver therapy to the patient, or provide some combination thereof.

Referring now to FIGS. 8 and 9, an example of an implantable cardiac device 800 (e.g., a stimulation device such as an implantable cardioverter defibrillator, a pacemaker, etc.) that may be configured to support neurostimulation operations in accordance with the teachings herein will be described. It is to be appreciated and understood that other cardiac devices, including those that are not necessarily implantable, may be used and that the description below is given, in its specific context, to assist the reader in understanding, with more clarity, sample uses of the embodiments described herein.

In various embodiments, the device 800 may be adapted to treat both fast and slow arrhythmias with stimulation therapy, including cardioversion, defibrillation, and pacing stimulation. While a particular multi-chamber device is shown, it is to be appreciated and understood that this is done for illustration purposes. Thus, the techniques and methods described below can be implemented in connection with any suitably configured or configurable device. Accordingly, one of skill in the art could readily duplicate, eliminate, or disable the appropriate circuitry in any desired combination to provide a device capable of treating the appropriate chamber(s) with, for example, cardioversion, defibrillation, and pacing stimulation.

FIG. 8 shows an exemplary implantable cardiac device 800 in electrical communication with a patient's heart H by way of three leads 804, 806, and 808, suitable for delivering multi-chamber stimulation and shock therapy. Bodies of the leads 804, 806, and 808 may be formed of silicone, polyurethane, plastic, or similar biocompatible materials to facilitate implant within a patient. Each lead includes one or more conductors, each of which may couple one or more electrodes incorporated into the lead to a connector on the proximal end of the lead. Each connector, in turn, is configured to couple with a complimentary connector (e.g., implemented within a header) of the device 800.

To sense atrial cardiac signals and to provide right atrial chamber stimulation therapy, the device 800 is coupled to an implantable right atrial lead 804 having, for example, an atrial tip electrode 820, which typically is implanted in the patient's right atrial appendage or septum. FIG. 8 also shows the right atrial lead 804 as having an optional atrial ring electrode 821.

To sense left atrial and ventricular cardiac signals and to provide left chamber pacing therapy, the device 800 is coupled to a coronary sinus lead 806 designed for placement in the coronary sinus region via the coronary sinus for positioning one or more electrodes adjacent to the left ventricle, one or more electrodes adjacent to the left atrium, or both. As used herein, the phrase "coronary sinus region" refers to the vasculature of the left ventricle, including any portion of the coronary sinus, the great cardiac vein, the left marginal vein, the left posterior ventricular vein, the middle cardiac vein, the small cardiac vein or any other cardiac vein accessible by the coronary sinus.

Accordingly, an exemplary coronary sinus lead 806 is designed to receive atrial and ventricular cardiac signals and to deliver left ventricular pacing therapy using, for example, a left ventricular tip electrode 822 and, optionally, a left ventricular ring electrode 823; provide left atrial pacing therapy using, for example, a left atrial ring electrode 824; and provide shocking therapy using, for example, a left atrial coil electrode 826 (or other electrode capable of delivering a shock). For a more detailed description of a coronary sinus lead, the reader is directed to U.S. Pat. No. 5,466,254, "Coronary Sinus Lead with Atrial Sensing Capability" (Helland), which is incorporated herein by reference.

The device 800 is also shown in electrical communication with the patient's heart H by way of an implantable right ventricular lead 808 having, in this implementation, a right ventricular tip electrode 828, a right ventricular ring electrode 830, a right ventricular (RV) coil electrode 832 (or other electrode capable of delivering a shock), and a superior vena cava (SVC) coil electrode 834 (or other electrode capable of delivering a shock). Typically, the right ventricular lead 808 is transvenously inserted into the heart H to place the right ventricular tip electrode 828 in the right ventricular apex so that the RV coil electrode 832 will be positioned in the right ventricle and the SVC coil electrode 834 will be positioned in the superior vena cava. Accordingly, the right ventricular lead 808 is capable of sensing or receiving cardiac signals, and delivering stimulation in the form of pacing and shock therapy to the right ventricle.

The device 800 is also shown in electrical communication with a lead 810 including one or more components 844. The component 844 may be positioned in, near or remote from the heart. For example, in some embodiments the component 844 may comprise a sensor. As another example, in embodiments where the device 800 comprises a neurostimulation circuit that generates neurostimulation signals, the lead 810 may comprise an implantable neurostimulation lead and the component 844 may comprise a neurostimulation electrode.

It should be appreciated that the device 800 may connect to leads other than those specifically shown. In addition, the leads connected to the device 800 may include components other than those specifically shown. For example, a lead may include other types of electrodes, sensors or devices that serve to otherwise interact with a patient or the surroundings.

FIG. 9 depicts an exemplary, simplified block diagram illustrating sample components of the device 800. The device 800 may be adapted to treat both fast and slow arrhythmias with stimulation therapy, including cardioversion, defibrillation, and pacing stimulation. While a particular multi-chamber device is shown, it is to be appreciated and understood that this is done for illustration purposes. Thus, the techniques and methods described below can be implemented in connection with any suitably configured or configurable device. Accordingly, one of skill in the art could readily duplicate, eliminate, or disable the appropriate circuitry in any desired combination to provide a device capable of treating the appropriate chamber(s) with, for example, cardioversion, defibrillation, and pacing stimulation.

A housing 900 for the device 800 is often referred to as the "can", "case" or "case electrode", and may be programmably selected to act as the return electrode for all "unipolar" modes. The housing 900 may further be used as a return electrode alone or in combination with one or more of the coil electrodes 826, 832 and 834 for shocking purposes. The housing 900 may be constructed of a biocompatible material (e.g., titanium) to facilitate implant within a patient.

The housing 900 further includes a connector (not shown) having a plurality of terminals 901, 902, 904, 905, 906, 908, 912, 914, 916 and 918 (shown schematically and, for convenience, the names of the electrodes to which they are connected are shown next to the terminals). The connector may be configured to include various other terminals (e.g., terminal 921 coupled to a sensor or some other component) depending on the requirements of a given application.

To achieve right atrial sensing and pacing, the connector includes, for example, a right atrial tip terminal (AR TIP) 902 adapted for connection to the right atrial tip electrode 820. A right atrial ring terminal (AR RING) 901 may also be included and adapted for connection to the right atrial ring electrode 821. To achieve left chamber sensing, pacing, and shocking, the connector includes, for example, a left ventricular tip terminal (VL TIP) 904, a left ventricular ring terminal (VL RING) 905, a left atrial ring terminal (AL RING) 906, and a left atrial shocking terminal (AL COIL) 908, which are adapted for connection to the left ventricular tip electrode 822, the left ventricular ring electrode 823, the left atrial ring electrode 824, and the left atrial coil electrode 826, respectively.

To support right chamber sensing, pacing, and shocking, the connector further includes a right ventricular tip terminal (VR TIP) 912, a right ventricular ring terminal (VR RING) 914, a right ventricular shocking terminal (RV COIL) 916, and a superior vena cava shocking terminal (SVC COIL) 918, which are adapted for connection to the right ventricular tip electrode 828, the right ventricular ring electrode 830, the RV coil electrode 832, and the SVC coil electrode 834, respectively.

At the core of the device 800 is a programmable microcontroller 920 that controls the various modes of stimulation therapy. As is well known in the art, microcontroller 920 typically includes a microprocessor, or equivalent control circuitry, designed specifically for controlling the delivery of stimulation therapy, and may further include memory such as RAM, ROM and flash memory, logic and timing circuitry, state machine circuitry, and I/O circuitry. Typically, microcontroller 920 includes the ability to process or monitor input signals (data or information) as controlled by a program code stored in a designated block of memory. The type of microcontroller is not critical to the described implementations. Rather, any suitable microcontroller 920 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals that may be used within the device and their inter-relationship, see U.S. Pat. No. 4,788,980 (Mann et al.), also incorporated herein by reference.

FIG. 9 also shows an atrial pulse generator 922 and a ventricular pulse generator 924 that generate pacing stimulation pulses for delivery by the right atrial lead 804, the coronary sinus lead 806, the right ventricular lead 808, or some combination of these leads via an electrode configuration switch 926. It is understood that in order to provide stimulation therapy in each of the four chambers of the heart, the atrial and ventricular pulse generators 922 and 924 may include dedicated, independent pulse generators, multiplexed pulse generators, or shared pulse generators. The pulse generators 922 and 924 are controlled by the microcontroller 920 via appropriate control signals 928 and 930, respectively, to trigger or inhibit the stimulation pulses.

Microcontroller 920 further includes timing control circuitry 932 to control the timing of the stimulation pulses (e.g., pacing rate, atrio-ventricular (A-V) delay, atrial interconduction (A-A) delay, or ventricular interconduction (V-V) delay, etc.) or other operations, as well as to keep track of the timing of refractory periods, blanking intervals, noise detection windows, evoked response windows, alert intervals, marker channel timing, etc., as known in the art.

Microcontroller 920 further includes an arrhythmia detector 934. The arrhythmia detector 934 may be utilized by the device 800 for determining desirable times to administer various therapies. The arrhythmia detector 934 may be implemented, for example, in hardware as part of the microcontroller 920, or as software/firmware instructions programmed into the device 800 and executed on the microcontroller 920 during certain modes of operation.

Microcontroller 920 may include a morphology discrimination module 936, a capture detection module 937 and an auto sensing module 938. These modules are optionally used to implement various exemplary recognition algorithms or methods. The aforementioned components may be implemented, for example, in hardware as part of the microcontroller 920, or as software/firmware instructions programmed into the device 800 and executed on the microcontroller 920 during certain modes of operation.

The electrode configuration switch 926 includes a plurality of switches for connecting the desired terminals (e.g., that are connected to electrodes, coils, sensors, etc.) to the appropriate I/O circuits, thereby providing complete terminal and, hence, electrode programmability. Accordingly, switch 926, in response to a control signal 942 from the microcontroller 920, may be used to determine the polarity of the stimulation pulses (e.g., unipolar, bipolar, combipolar, etc.) by selectively closing the appropriate combination of switches (not shown) as is known in the art.

Atrial sensing circuits (ATR. SENSE) 944 and ventricular sensing circuits (VTR. SENSE) 946 may also be selectively coupled to the right atrial lead 804, coronary sinus lead 806, and the right ventricular lead 808, through the switch 926 for detecting the presence of cardiac activity in each of the four chambers of the heart. Accordingly, the atrial and ventricular sensing circuits 944 and 946 may include dedicated sense amplifiers, multiplexed amplifiers, or shared amplifiers. Switch 926 determines the "sensing polarity" of the cardiac signal by selectively closing the appropriate switches, as is also known in the art. In this way, the clinician may program the sensing polarity independent of the stimulation polarity. The sensing circuits (e.g., circuits 944 and 946) are optionally capable of obtaining information indicative of tissue capture.

Each sensing circuit 944 and 946 preferably employs one or more low power, precision amplifiers with programmable gain, automatic gain control, bandpass filtering, a threshold detection circuit, or some combination of these components, to selectively sense the cardiac signal of interest. The automatic gain control enables the device 800 to deal effectively with the difficult problem of sensing the low amplitude signal characteristics of atrial or ventricular fibrillation.

The outputs of the atrial and ventricular sensing circuits 944 and 946 are connected to the microcontroller 920, which, in turn, is able to trigger or inhibit the atrial and ventricular pulse generators 922 and 924, respectively, in a demand fashion in response to the absence or presence of cardiac activity in the appropriate chambers of the heart. Furthermore, as described herein, the microcontroller 920 is also capable of analyzing information output from the sensing circuits 944 and 946, a data acquisition system 952, or both. This information may be used to determine or detect whether and to what degree tissue capture has occurred and to program a pulse, or pulses, in response to such determinations. The sensing circuits 944 and 946, in turn, receive control signals over signal lines 948 and 950, respectively, from the microcontroller 920 for purposes of controlling the gain, threshold, polarization charge removal circuitry (not shown), and the timing of any blocking circuitry (not shown) coupled to the inputs of the sensing circuits 944 and 946 as is known in the art.

For arrhythmia detection, the device 800 utilizes the atrial and ventricular sensing circuits 944 and 946 to sense cardiac signals to determine whether a rhythm is physiologic or pathologic. It should be appreciated that other components may be used to detect arrhythmia depending on the system objectives. In reference to arrhythmias, as used herein, "sensing" is reserved for the noting of an electrical signal or obtaining data (information), and "detection" is the processing (analysis) of these sensed signals and noting the presence of an arrhythmia.

Timing intervals between sensed events (e.g., P-waves, R-waves, and depolarization signals associated with fibrillation) may be classified by the arrhythmia detector 934 of the microcontroller 920 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules may be applied to the atrial channel to determine if there is an atrial tachyarrhythmia or atrial fibrillation with appropriate classification and intervention.

Cardiac signals or other signals may be applied to inputs of an analog-to-digital (ND) data acquisition system 952. The data acquisition system 952 is configured (e.g., via signal line 956) to acquire intracardiac electrogram ("IEGM") signals or other signals, convert the raw analog data into a digital signal, and store the digital signals for later processing, for telemetric transmission to an external device 954, or both. For example, the data acquisition system 952 may be coupled to the right atrial lead 804, the coronary sinus lead 806, the right ventricular lead 808 and other leads through the switch 926 to sample cardiac signals across any pair of desired electrodes.

The data acquisition system 952 also may be coupled to receive signals from other input devices. For example, the data acquisition system 952 may sample signals from a physiologic sensor 970 or other components shown in FIG. 9 (connections not shown).

The microcontroller 920 is further coupled to a memory 960 by a suitable data/address bus 962, wherein the programmable operating parameters used by the microcontroller 920 are stored and modified, as required, in order to customize the operation of the device 800 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart H within each respective tier of therapy. One feature of the described embodiments is the ability to sense and store a relatively large amount of data (e.g., from the data acquisition system 952), which data may then be used for subsequent analysis to guide the programming of the device 800.

Advantageously, the operating parameters of the implantable device 800 may be non-invasively programmed into the memory 960 through a telemetry circuit 964 in telemetric communication via communication link 966 with the external device 954, such as a programmer, transtelephonic transceiver, a diagnostic system analyzer or some other device. The microcontroller 920 activates the telemetry circuit 964 with a control signal (e.g., via bus 968). The telemetry circuit 964 advantageously allows intracardiac electrograms and status information relating to the operation of the device 800 (as contained in the microcontroller 920 or memory 960) to be sent to the external device 954 through an established communication link 966.

The device 800 can further include one or more physiologic sensors 970. In some embodiments, the device 800 may include a "rate-responsive" sensor that may provide, for example, information to aid in adjustment of pacing stimulation rate according to the exercise state of the patient. One or more physiologic sensors 970 (e.g., a pressure sensor) may further be used to detect changes in cardiac output, changes in the physiological condition of the heart, or diurnal changes in activity (e.g., detecting sleep and wake states). Accordingly, the microcontroller 920 responds by adjusting the various pacing parameters (such as rate, A-V Delay, V-V Delay, etc.) at which the atrial and ventricular pulse generators 922 and 924 generate stimulation pulses.

While shown as being included within the device 800, it is to be understood that a physiologic sensor 970 may also be external to the device 800, yet still be implanted within or carried by the patient. Examples of physiologic sensors that may be implemented in conjunction with the device 800 include sensors that sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), which patent is hereby incorporated by reference.

The one or more physiologic sensors 970 may optionally include one or more of components to help detect movement (via, e.g., a position sensor or an accelerometer) and minute ventilation (via an MV sensor) in the patient. Signals generated by the position sensor and MV sensor may be passed to the microcontroller 920 for analysis in determining whether to adjust the pacing rate, etc. The microcontroller 920 may thus monitor the signals for indications of the patient's position and activity status, such as whether the patient is climbing up stairs or descending down stairs or whether the patient is sitting up after lying down.

The device 800 additionally includes a battery 976 that provides operating power to all of the circuits shown in FIG. 9. For a device 800 which employs shocking therapy, the battery 976 is capable of operating at low current drains (e.g., preferably less than 10 μA) for long periods of time, and is capable of providing high-current pulses (for capacitor charging) when the patient requires a shock pulse (e.g., preferably, in excess of 2 A, at voltages above 200 V, for periods of 10 seconds or more). The battery 976 also desirably has a predictable discharge characteristic so that elective replacement time can be detected. Accordingly, the device 800 preferably employs lithium or other suitable battery technology.

The device 800 can further include magnet detection circuitry (not shown), coupled to the microcontroller 920, to detect when a magnet is placed over the device 800. A magnet may be used by a clinician to perform various test functions of the device 800 and to signal the microcontroller 920 that the external device 954 is in place to receive data from or transmit data to the microcontroller 920 through the telemetry circuit 964.

The device 800 further includes an impedance measuring circuit 978 that is enabled by the microcontroller 920 via a control signal 980. The known uses for an impedance measuring circuit 978 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device 800 has been implanted; measuring stroke volume; and detecting the opening of heart valves, etc. The impedance measuring circuit 978 is advantageously coupled to the switch 926 so that any desired electrode may be used.

In the case where the device 800 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 920 further controls a shocking circuit 982 by way of a control signal 984. The shocking circuit 982 generates shocking pulses of low (e.g., up to 0.5 J), moderate (e.g., 0.5 J to 10 J), or high energy (e.g., 11 J to 40 J), as controlled by the microcontroller 920. Such shocking pulses are applied to the patient's heart H through, for example, two shocking electrodes and as shown in this embodiment, selected from the left atrial coil electrode 826, the RV coil electrode 832 and the SVC coil electrode 834. As noted above, the housing 900 may act as an active electrode in combination with the RV coil electrode 832, as part of a split electrical vector using the SVC coil electrode 834 or the left atrial coil electrode 826 (i.e., using the RV electrode as a common electrode), or in some other arrangement.

Cardioversion level shocks are generally considered to be of low to moderate energy level (so as to minimize pain felt by the patient), be synchronized with an R-wave, pertain to the treatment of tachycardia, or some combination of the above. Defibrillation shocks are generally of moderate to high energy level (i.e., corresponding to thresholds in the range of 5 J to 40 J), delivered asynchronously (since R-waves may be too disorganized), and pertaining to the treatment of fibrillation. Accordingly, the microcontroller 920 is capable of controlling the synchronous or asynchronous delivery of the shocking pulses.

As mentioned above, the device 800 may include several components that provide neurostimulation-related functionality as taught herein. For example, one or more of the switch 926, the sense circuits 944, 946, and the data acquisition system 952 may acquire cardiac signals that are used in the cardiac condition monitoring operations discussed above. The data described above may be stored in the data memory 960. In addition, a warning/therapy module 940 may be configured to generate warning signals based on the assessment of cardiac risk and, in the case of an implantable stimulation device, facilitate the administration of therapy.

The microcontroller 920 (e.g., a processor providing signal processing functionality) also may implement or support at least a portion of the neurostimulation-related functionality discussed herein. For example, a neurostimulation control component 939 may perform cardiovascular risk assessment operations, stimulation adaptation operations, and stimulation triggering operations as described above. In addition, in the case of an implantable stimulation device, a stimulation circuit 986 may generate neurostimulation signals that are output via one or more terminals (e.g., STIM. terminal 921).

It should be appreciated that various modifications may be incorporated into the disclosed embodiments based on the teachings herein. For example, the structure and functionality taught herein may be incorporated into types of devices other than the specific types of devices described above.

In addition, the functionality described herein may be implemented in a variety of ways. For example, a neurostimulation control (e.g., trigger) may take various forms. In some embodiments, an implantable medical device generates pacing pulses to trigger neurostimulation. For example, a cardiac pacing circuit of the device may be configured to generate a plurality of pacing pulses during a cardiac refractory period (to prevent actual pacing) as a result of receiving a control indication from a processing circuit of the apparatus. Here, the timing and/or other characteristics of the pacing pulses may be uniquely configured to unambiguously indicate to an implanted neurostimulation device (configured to monitor for such pacing pulses) that neurostimulation is to be commenced. Thus, in such a case, the implantable medical device and the implantable neurostimulation device need not be configured to establish formal communication with one another.

Different embodiments of an apparatus (e.g., device) as taught herein may include a variety of hardware and software processing components. In some embodiments, hardware components such as processors, controllers, state machines, logic, or some combination of these components, may be used to implement the described components or circuits.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

Moreover, some of the operations described herein may be performed by a device that is located externally with respect to the body of the patient. For example, an implanted device may send raw data or processed data to an external device that then performs the necessary processing.

The components and functions described herein may be connected or coupled in many different ways. The manner in which this is done may depend, in part, on whether and how the components are separated from the other components. In some embodiments, some of the connections or couplings represented by the lead lines in the drawings may be in an integrated circuit, on a circuit board or implemented as discrete wires or in other ways.

The signals discussed herein may take various forms. For example, in some embodiments a signal may comprise electrical signals transmitted over a wire, light pulses transmitted through an optical medium such as an optical fiber or air, or RF waves transmitted through a medium such as air, and so on. In addition, a plurality of signals may be collectively referred to as a signal herein. The signals discussed above also may take the form of data. For example, in some embodiments an application program may send a signal to another application program. Such a signal may be stored in a data memory.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

Also, it should be understood that any reference to elements herein using a designation such as "first," "second," and so forth does not generally limit the quantity or order of those elements. Rather, these designations may be used herein as a convenient method of distinguishing between two or more different elements or instances of an element. Thus, a reference to first and second elements does not mean that only two elements may be employed there or that the first element must precede the second element in some manner. Also, unless stated otherwise a set of elements may comprise one or more elements. In addition, terminology of the form "at least one of A, B, or C" or "one or more of A, B, or C" or "at least one of the group consisting of A, B, and C" used in the description or the claims means "A or B or C or any combination of these elements." For example, this terminology may include A, or B, or C, or A and B, or A and C, or A and B and C, or 2A, or 2B, or 2C, and so on.

As used herein, the term "determining" encompasses a wide variety of actions. For example, "determining" may include calculating, computing, processing, deriving, investigating, looking up (e.g., looking up in a table, a database or another data structure), ascertaining, and the like. Also, "determining" may include receiving (e.g., receiving information), accessing (e.g., accessing data in a memory), and the like. Also, "determining" may include resolving, selecting, choosing, establishing, and the like.

In some aspects, an apparatus or any component of an apparatus may be configured to (or operable to or adapted to) provide functionality as taught herein. This may be achieved, for example: by manufacturing (e.g., fabricating) the apparatus or component so that it will provide the functionality; by programming the apparatus or component so that it will provide the functionality; or through the use of some other suitable implementation technique.

While certain embodiments have been described above in detail and shown in the accompanying drawings, it is to be understood that such embodiments are merely illustrative of and not restrictive of the teachings herein. In particular, it should be recognized that the teachings herein apply to a wide variety of apparatuses and methods. It will thus be recognized that various modifications may be made to the illustrated embodiments or other embodiments, without departing from the broad scope thereof. In view of the above, it will be understood that the teachings herein are intended to cover any changes, adaptations or modifications that are within the scope of the disclosure.

What is claimed is:

1. An implantable medical device, comprising:
a receiver circuit configured to acquire cardiac signals of a patient; and
a processing circuit configured to process the acquired cardiac signals to detect an ischemic event, and to control application of neurostimulation to the patient based on the detection of the ischemic event, wherein:
the receiver circuit is further configured to acquire additional cardiac signals after the neurostimulation is applied to the patient, and
the processing circuit is further configured to determine if the ischemic event is terminated based on the acquired additional cardiac signals, and to adapt neurostimulation to the patient based on the determination, wherein the processing circuit is further configured to control the receiver circuit and the application of the neurostimulation to prevent acquisition of the cardiac signals during neurostimulation.

2. The implantable medical device of claim 1, wherein the controlling of the application of neurostimulation comprises triggering the application of neurostimulation.

3. The implantable medical device of claim 1, wherein the controlling of the application of neurostimulation comprises adjusting at least one parameter of neurostimulation.

4. The implantable medical device of claim 1, wherein the assessment and reassessment of cardiovascular risk comprises at least one of: detecting a change in an ST segment, detecting cardiac rate variability, detecting T-wave alternans, detecting cardiac ectopy, detecting a change in QRS morphology, or detecting a change in left-right chamber synchrony.

5. The implantable medical device of claim 1, wherein the neurostimulation comprises: spinal cord stimulation, vagus nerve stimulation, baroreceptor stimulation, or subcutaneous nerve stimulation.

6. The implantable medical device of claim 1, wherein:
the receiver circuit is further configured to detect neurostimulation signals; and
the processing circuit is further configured to disable the acquisition of the cardiac signals as a result of the detection of the neurostimulation signals.

7. The implantable medical device of claim 1, wherein:
the assessment of cardiovascular risk or the reassessment of cardiovascular risk comprises classifying cardiovascular risk according to a plurality of cardiovascular risk levels; and
the controlling of the neurostimulation comprises triggering different neurostimulation operations based on the classification.

8. The implantable medical device of claim 7, wherein the different neurostimulation operations involve use of different neurostimulation signals.

9. The implantable medical device of claim 7, wherein the different neurostimulation operations involve use of different neurostimulation electrodes.

10. The implantable medical device of claim 7, wherein at least one of the risk levels is associated with notifying the patient of cardiovascular risk.

11. The implantable medical device of claim 7, wherein at least one of the risk levels is associated with the application of neurostimulation that is not perceivable by the patient.

12. The implantable medical device of claim 1, wherein:
the controlling of the application of the neurostimulation comprises generating a control indication;
the implantable medical device further comprises a communication circuit configured to transmit a message that controls the neurostimulation to a neurostimulation device; and
the communication circuit is further configured to transmit the message as a result of receiving the control indication from the processing circuit.

13. The implantable medical device of claim 1, wherein:
the controlling of the application of the neurostimulation comprises generating a control indication; and
the implantable medical device further comprises a stimulation circuit configured to generate a neurostimulation signal to provide the neurostimulation as a result of receiving the control indication from the processing circuit.

14. The implantable medical device of claim 1, wherein:
the controlling of the application of the neurostimulation comprises generating a control indication;
the implantable medical device further comprises a cardiac pacing circuit configured to generate pacing pulses; and
the cardiac pacing circuit is configured to generate a plurality of pacing pulses during a cardiac refractory period as a result of receiving the control indication from the processing circuit.

15. An implantable medical device, comprising:
a receiver circuit configured to acquire cardiac signals of a patient; and
a processing circuit configured to process the acquired cardiac signals to detect an ischemic event, and to control application of neurostimulation to the patient based on the detection of the ischemic event, wherein:

the receiver circuit is further configured to acquire additional cardiac signals after the neurostimulation is applied to the patient, the processing circuit is further configured to determine if the ischemic event is terminated based on the acquired additional cardiac signals, and to adapt neurostimulation to the patient based on the determination; and a communication circuit, wherein the processing circuit is further configured to communicate with a neurostimulation device via the communication circuit to disable neurostimulation during acquisition of the cardiac signals.

16. An implantable medical device, comprising:

a receiver circuit configured to acquire cardiac signals of a patient; and a processing circuit configured to detect at least one change in an ST segment based on the acquired cardiac signals, classifying the at least one change in an ST segment according to a plurality of cardiovascular risk levels and further configured to control application of neurostimulation to the patient based on the detected at least one change in the ST segment and the classification of cardiovascular risk level, the processing circuit being further configured to prevent acquisition of the cardiac signals during neurostimulation.

17. The implantable medical device of claim 16, wherein:

the controlling of the neurostimulation comprises triggering different neurostimulation operations based on the classification.

18. The implantable medical device of claim 16, wherein the neurostimulation comprises: spinal cord stimulation, vagus nerve stimulation, baroreceptor stimulation, or subcutaneous nerve stimulation.

* * * * *